United States Patent
Mattes et al.

(10) Patent No.: US 7,947,378 B2
(45) Date of Patent: May 24, 2011

(54) MEDICAL ASSEMBLY SUITABLE FOR LONG-TERM IMPLANTATION AND METHOD FOR FABRICATING THE SAME

(75) Inventors: Michael F. Mattes, Chandler, AZ (US); Alvin S. Rhorer, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/906,262

(22) Filed: Oct. 18, 2010

(65) Prior Publication Data

US 2011/0034825 A1  Feb. 10, 2011

Related U.S. Application Data

(60) Division of application No. 11/351,050, filed on Feb. 9, 2006, now Pat. No. 7,838,119, which is a continuation-in-part of application No. 10/246,857, filed on Sep. 19, 2002, now Pat. No. 7,025,982.

(51) Int. Cl.
*B32B 27/30* (2006.01)

(52) U.S. Cl. ......... 428/500; 428/448; 428/450; 428/451
(58) Field of Classification Search .................. 428/448, 428/450, 451, 500
See application file for complete search history.

(56) References Cited

U.S. PATENT DOCUMENTS

| | | |
|---|---|---|
| 5,415,619 A | 5/1995 | Lee et al. |
| 6,743,521 B2 | 6/2004 | Hubbell et al. |
| 2004/0057978 A1 | 3/2004 | Mattes et al. |
| 2005/0131531 A1 | 6/2005 | Keenan |

*Primary Examiner* — D. S Nakarani

(57) ABSTRACT

A process for fabricating a medical assembly having a medical device at least a portion of which is formed of inorganic material is provided. The medical assembly is suitable for substantially long-term implantation in a host animal. The process includes modifying a surface of the medical device to form a hydrophilic adhesion-promoting surface. The hydrophilic adhesion-promoting surface is coated with an alginate solution comprising alginate and the alginate is reacted with alkaline earth metal cations.

11 Claims, 2 Drawing Sheets

MEDICAL ASSEMBLY SUITABLE FOR LONG-TERM IMPLANTATION AND METHOD FOR FABRICATING THE SAME

PRIOR APPLICATION

This application is a divisional of U.S. patent application Ser. No. 11/351,050, filed Feb. 9, 2006, now U.S. Pat. No. 7,838,119 now allowed, which is a continuation-in-part application of U.S. Ser. No. 10/246,857, filed Sep. 19, 2002, now U.S. Pat. No. 7,025,982, which is incorporated herein by reference in its entirety.

FIELD OF THE INVENTION

This invention relates generally to implantable medical devices and more specifically to medical devices coated with alginate material for long-term implantation into living tissue of a host and methods of making the same.

BACKGROUND OF THE INVENTION

Medical treatments for the shortcomings or functional deficiencies of biological organs and systems have long included the implantation of inorganic medical devices or the implantation of medical devices that are formed, at least in part, of inorganic materials. Such medical devices are designed to restore or replace a useful biological function needed by the host animal. Implantable medical devices have been designed to perform a variety of biological functions, including, without limitation, restoring the functioning of a failed heart, monitoring the chemical or electrical stimuli produced by a system or organ, secreting needed synthetic pharmaceutical compositions, and draining undesirable fluids from organs or tissues. Implantable devices such as catheters, stents, fluid flow control valves, biosensors, pressure sensors, pacemakers and the like are well known in the medical industry.

The implantation of such device for long periods of time, that is, on the order of months or years, has often proven unsuccessful due to rejection by the immunological system of the host animal, particularly as a result of fibrous tissue growth. Fibrous tissue growth can impair the operation of certain devices such as, for example, sensors. Fibrous tissue growth can also reduce the efficiency of devices such as electrodes in pacing devices and antennas in in-vivo telemetry systems.

Current solutions for the prevention of fibrous tissue growth on implanted devices have included the use of timed releasable drugs or molecules, such as heparin or other antibiotics and antithrombogenics. However, such methods typically have proven to be short-term solutions, that is, on the order of days to months. In addition, the use of such drugs is costly, may have deleterious effects on the immune system of the host animal, and may subject the host animal to the side effects of the drugs.

Accordingly, a need exists for a medical device suitable for long-term implantation in a host animal. A need also exists for a process for fabricating a medical device suitable for long-term implantation in a host animal.

BRIEF DESCRIPTION OF THE DRAWINGS

The present invention is illustrated by way of example and not limitation in the accompanying figures, in which like references indicate similar elements, and in which.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims. In accordance with one embodiment, a medical assembly suitable for substantially long-term implantation in a host animal is provided. The medical assembly includes a medical device at least a portion of which is formed of inorganic material. The medical assembly also includes a hydrophilic adhesion-promoting surface formed on the medical device and a gelled alginate coating overlying the hydrophilic adhesion-promoting surface.

Figure 1:
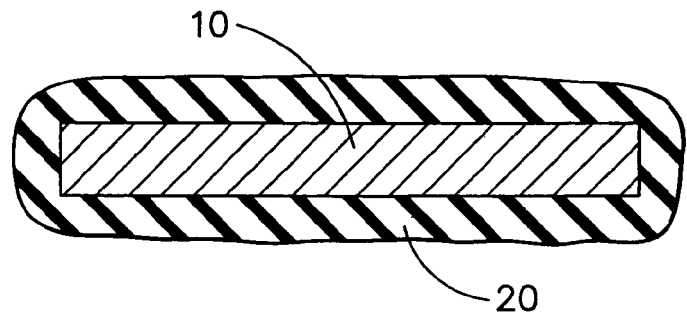
FIG. 1. is a cross-sectional view of a medical device coated with a biocompatible material.

FIGS. 1-4 illustrate a process in accordance with one exemplary embodiment of the invention for making a medical assembly that is suitable for long-term implantation in a host animal. Referring to FIG. 1, a medical device 10 is provided. Medical device 10 may include any mechanism that performs or provides a useful biological function. At least a portion of medical device 10 is formed of inorganic material, although it will be appreciated that medical device 10 may also comprise any suitable amount of organic matter. Medical device 10 may include, without limitation, pressure sensors, biosensors, actuators, catheters, stents, fluid flow control valves, such as cerebral spinal fluid flow control valves, microelectromechanical systems, nanoelectromechanical systems, and the like. Medical device 10 may also include any suitable packaging, material or protected manufacturing environment for in-vivo biological factories.

In accordance with one exemplary embodiment of the invention, a surface of medical device 10 may be treated to render the surface more adhesive to later-applied materials, as described in more detail below. One exemplary method for rendering a surface of medical device 10 more adhesive includes coating medical device 10 with a biocompatible polymer coating 20 that renders the surface of medical device 10 more adhesive to later-applied materials, as illustrated in FIG. 1. Biocompatible polymer coating 20 may also serve to round any sharp, pointed, rough or otherwise problematic areas of medical device 10 that, without such coating, would otherwise lead to fibrosis or thrombosis. One example of material suitable for forming biocompatible polymer coating 20 is silicone, although it will be appreciated that any other suitable polymer that is biocompatible with the host animal and renders the surface of medical device 10 more adhesive may be used.

Another exemplary method for rendering a surface of medical device 10 more adhesive includes oxidizing medical device 10 or coating medical device 10 with a material which can be oxidized to render it more readily adhesive to later-applied materials. For example, if medical device 10 is formed on a silicon wafer, such as in the case of certain pressure sensors, medical device 10 may be oxidized to form a silicon dioxide layer on its surface. The silicon dioxide surface of medical device 10 permits adhesion of later-applied materials while also rendering medical device 10 hydrophilic.

It will be appreciated that the entire surface of medical device 10 or, alternatively, only portions or components of the surface of medical device 10 may be treated to enhance adhesiveness. The type and design of medical device used, the materials from which the medical device is made and the desired duration of implantation in the host animal may all be factors that determine the amount and positioning of surface to be treated.

Figure 2:
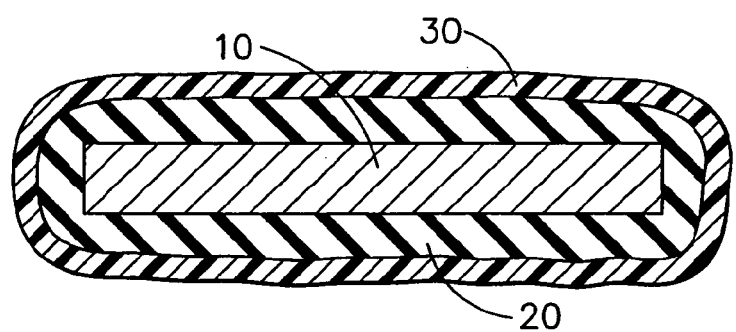
FIG. 2 is a cross-sectional view of the medical device of FIG. 1 comprising a hydrophilic adhesion-promoting surface.

As illustrated in FIG. 2, the surface of medical device 10 then is modified to form a hydrophilic adhesion-promoting surface 30. Hydrophilic adhesion-promoting surface 30 allows ready adhesion of the subsequently-applied alginate material, described in more detail below, and provides a biocompatible hydrophilic surface. In one exemplary embodiment, the surface of medical device 10 may be modified to form hydrophilic adhesion-promoting surface 30 by applying an adhesion-promoting material that promotes adhesion between medical device 10 (and/or biocompatible polymer coating 20) and a later-applied alginate material, discussed in more detail below. The adhesion-promoting material may be applied by any suitable method that permits controlled, even distribution of the adhesion-promoting material on medical device 10. For example, the adhesion-promoting material may be spray-coated onto medical device 10 or may be brush-coated onto medical device 10. Alternatively, medical device 10 may be suspended or immersed in the adhesion-promoting material. In a further example, the adhesion-promoting material may be vaporized and permitted to be deposited on a desired surface of medical device 10. It will be appreciated that any other suitable method for applying the adhesion-promoting material to medical device 10 may be used. It will further be appreciated that the adhesion-promoting material may deposited on all surfaces or, alternatively, on only selected surfaces of medical device 10 as may be suitable for a desired application or medical device. One example of a material that is suitable for forming hydrophilic adhesion-promoting surface 30 is N, N-diethylaminotrimethylsilane ("DEATS"), available from suppliers such as MicroSi, Inc. of Phoenix, Ariz. DEATS is a low viscosity organosilane typically used as a photoresist adhesion promoter. Another example of a material that is suitable for forming hydrophilic adhesion-promoting surface 30 is polyvinyl pyrrolidone (PVP), such as that available from Parchem Trading Ltd. of White Plains, N.Y. It will be appreciated that any other material suitable for forming a biocompatible hydrophilic adhesion-promoting surface, or any suitable combination or layering of such materials to form a biocompatible hydrophilic adhesion-promoting surface, may also be used.

In another exemplary embodiment of the invention, the surface of medical device 10 may be modified to form hydrophilic adhesion-promoting surface 30 by subjecting biocompatible polymer 20 to plasma bombardment. Plasma bombardment of polymers for enhanced adhesion bonding is well known in the polymer industry. Plasma bombardment is performed such that at least the surface of polymer 20 is altered chemically to provide improved adhesive properties. In yet another exemplary embodiment of the invention, medical device 10 may be coated with an additional biocompatible polymer, which is subsequently subjected to plasma bombardment. One example of a biocompatible polymer that may be subjected to plasma bombardment to form surface 30 includes, without limitation, polytetraflouroethylene (PTFE).

Figure 3:
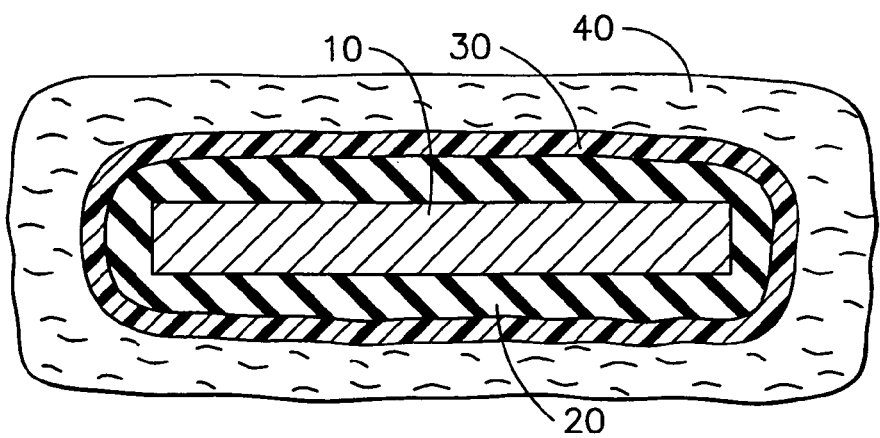
FIG. 3 is a cross-sectional view of the medical device of FIG. 2 coated with an alginate material.

Referring to FIG. 3, once hydrophilic adhesion-promoting surface 30 had been formed on medical device 10, medical device 10 may be subjected to an alginate solution to coat it with an alginate coating 40. Alginate is obtained from seaweed and is a linear unbranched polymer containing (1-4)-linked β-D-mannuronic acid and α-L-guluronic acid residues. Changes in the physical properties of alginate in the presence of various ions are exploited in the exemplary embodiments of the present invention. In the presence of monovalent counter ions such as sodium and potassium, alginate solutions are liquid. In the presence of multivalent cations such as calcium, barium and zinc, the alginate forms a gel. The alginate solution may include any alginate capable of forming a non-fibrogenic, gelled coating on or around medical device 10. In a preferred embodiment of the invention, the alginate solution is formed of a low viscosity sodium alginate.

In another exemplary embodiment of the present invention, before medical device 10 is subjected to the alginate solution, the alginate solution may be purified to remove particulates, fucose, organic contaminants such as polyphenols, and other fibrosis-generating components. One exemplary method for purifying sodium alginate is disclosed in U.S. Pat. No. 5,429, 821 issued Jul. 4, 1995 to Dorian et al.

The medical device 10 may be subjected to the alginate solution by any method that permits the hydrophilic adhesion promoting surface 30 of medical device 10 to be coated by the alginate material. It will be appreciated that the alginate material may be deposited to coat entire medical device 10 or to coat only portions of medical device 10 depending on the surfaces of medical device 10 treated to form hydrophilic adhesion-promoting surface 30.

It also will be appreciated that the alginate solution may be applied to the hydrophilic adhesion promoting surface 30 of medical device 10 by any method suitable for appropriately coating hydrophilic adhesion promoting surface 30 with alginate material. For example, in one exemplary embodiment of the present invention, medical device 10 may be suspended in the alginate solution for an appropriate amount of time to allow for suitable coating of medical device 10 by the alginate material. In another embodiment of the present invention, medical device 10 may be spray-coated with the alginate solution. In yet another embodiment of the present invention, the alginate solution may be brushed or "painted" on medical device 10.

Figure 4:
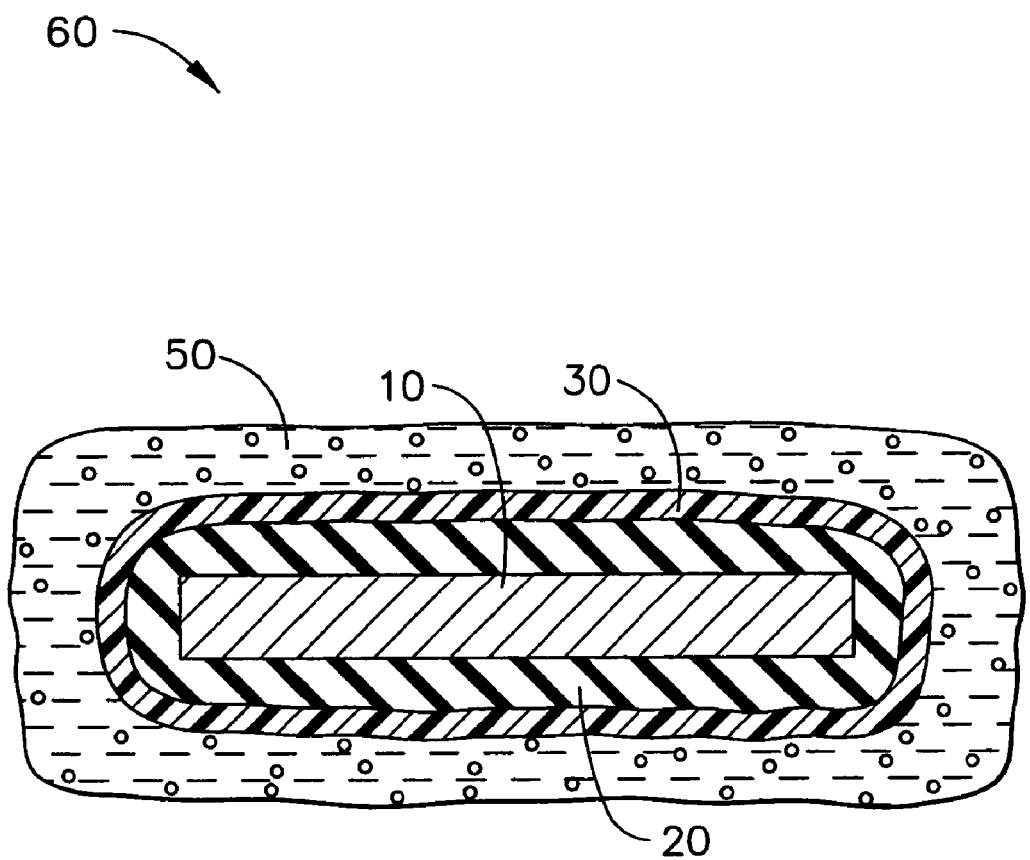
FIG. 4 is a cross-sectional view of the medical device of FIG. 3 coated with a gelled alginate.

Referring to FIG. 4, medical device 10 then is contacted with a suitable gelling solution to form a gelled alginate coating 50, thereby forming medical assembly 60. The gelling solution includes alkaline earth metal cations, such as calcium, barium, zinc and the like, that result in the gelling of the alginate material. In one exemplary embodiment of the present invention, the gelling solution includes calcium chloride or barium chloride. In a preferred embodiment of the present invention, the alginate coating is gelled by subjecting medical device 10 first to a solution of calcium chloride and then to a solution of barium chloride. Without being limited by any particular theory, it is believed that in this preferred embodiment the calcium cross-links with the guluronic acid blocks of the alginate molecules, and the barium cross-links with the mannuronic block of the alginate molecules and the guluronic portions which have not previously been cross-linked with the calcium chloride.

Medical device 10 may be contacted with the gelling solution by any suitable method, such as by submerging medical device 10 in the gelling solution, spray-coating medical device 10 with the gelling solution, and brush-coating medical device 10 with the gelling solution. It will be appreciated, however, that gelling solution may be applied to medical device 10 by any other method suitable for appropriately gelling the alginate material.

It will now be appreciated that medical assembly 60 of the present invention is configured to be implanted into the body of a host animal for long durations, typically on the order of from hours to years, without the negative effects caused by fibrous tissue growth and immunological rejection. According to various embodiments of the medical assembly of the present invention, as described above, the medical assembly comprises a medical device that is coated or encapsulated in a gelled alginate material. The gelled alginate material renders the medical device effectively "bioinvisible," that is, the medical device becomes a substantially systemically, pharmacologically inert substance with the deleterious effects from fibrosis substantially reduced or eliminated.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential features or elements of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A medical assembly suitable for substantially long-term implantation in a host animal, the medical assembly comprising:
    a medical device at least a portion of which is formed of inorganic material;
    a hydrophilic adhesion-promoting surface comprising polyvinyl pyrrolidone formed on said medical device; and
    a gelled alginate coating overlying said hydrophilic adhesion-promoting surface, wherein the medical assembly relates to a sensor.

2. The medical assembly of claim 1, said medical device having an oxidized surface underlying said hydrophilic adhesion-promoting surface.

3. The medical assembly of claim 1, said hydrophilic adhesion-promoting surface subjected to plasma bombardment.

4. The medical assembly of claim 1, said gelled alginate coating comprising an additional biocompatible material subjected to plasma bombardment.

5. The medical assembly of claim 1, said gelled alginate formed from a sodium alginate solution.

6. The medical assembly of claim 1, said gelled alginate formed by applying an alginate solution to said hydrophilic adhesion-promoting surface and contacting said alginate solution with a gelling solution comprising alkaline earth metal cations.

7. The medical assembly of claim 6, said alkaline earth metal cations comprising at least one of calcium and barium ions.

8. The medical assembly of claim 6, said gelled alginate formed by applying said alginate solution to said hydrophilic adhesion-promoting surface, contacting said alginate solution with a gelling solution comprising calcium chloride and then contacting said alginate solution with a gelling solution comprising barium chloride.

9. The medical assembly of claim 1 wherein the sensor being one of a pressure sensor, pH sensor, temperature sensor or flow sensor.

10. A medical assembly suitable for substantially long-term implantation in a host animal, the medical assembly comprising:
    a medical device at least a portion of which is formed of inorganic material;
    a hydrophilic adhesion-promoting surface comprising polyvinyl pyrrolidone formed on said medical device; and
    a gelled alginate coating overlying said hydrophilic adhesion-promoting surface, wherein the medical assembly relates to a biosensor, an actuator, a catheter, a stent, a fluid flow control valve, a microelectromechanical system, and a nanoelectromechanical system.

11. The medical assembly of claim 10 wherein the fluid flow control valve being a cerebral spinal fluid flow control valve.

* * * * *